(12) United States Patent
Dillingham

(10) Patent No.: US 8,491,667 B2
(45) Date of Patent: Jul. 23, 2013

(54) MODULAR PROSTHESIS SYSTEM

(76) Inventor: Timothy R Dillingham, Merion Station, PA (US)

(*) Notice: Subject to any disclaimer, the term of this patent is extended or adjusted under 35 U.S.C. 154(b) by 181 days.

(21) Appl. No.: 13/083,403

(22) Filed: Apr. 8, 2011

(65) Prior Publication Data

US 2012/0259433 A1   Oct. 11, 2012

(51) Int. Cl.
*A61F 2/80* (2006.01)
*A61F 2/78* (2006.01)

(52) U.S. Cl.
USPC ................................. 623/32; 623/36; 623/38

(58) Field of Classification Search
USPC ................................................. 623/32, 36, 38
See application file for complete search history.

(56) References Cited

U.S. PATENT DOCUMENTS

| | | | |
|---|---|---|---|
| 1,090,881 A | 3/1914 | Rowley | |
| 4,161,042 A | 7/1979 | Cottingham et al. | |
| 4,302,856 A | 12/1981 | May | |
| 4,872,879 A | 10/1989 | Shamp | |
| 5,314,497 A | 5/1994 | Fay et al. | |
| 5,425,782 A * | 6/1995 | Phillips | 623/38 |
| 5,443,526 A | 8/1995 | Hoerner | |
| 5,529,575 A | 6/1996 | Klotz | |
| 5,571,209 A | 11/1996 | Brown, Sr. | |
| 5,651,792 A | 7/1997 | Telikicherla | |
| 5,728,165 A | 3/1998 | Brown, Sr. | |
| 5,728,170 A | 3/1998 | Becker et al. | |
| 5,888,234 A | 3/1999 | Littig | |
| 5,941,912 A | 8/1999 | Taylor et al. | |
| 6,051,026 A | 4/2000 | Biedermann et al. | |
| 6,267,787 B1 | 7/2001 | Capper et al. | |
| 6,398,817 B1 | 6/2002 | Hellberg et al. | |
| 6,689,171 B2 | 2/2004 | Slemker et al. | |
| 6,942,703 B2 | 9/2005 | Carstens | |
| 6,991,657 B1 | 1/2006 | Price, Jr. | |
| 7,083,654 B2 | 8/2006 | Helenberger et al. | |
| D617,460 S | 6/2010 | Okuda et al. | |
| 2002/0116789 A1 | 8/2002 | McDevitt | |
| 2003/0023320 A1 | 1/2003 | Laghi | |
| 2003/0233151 A1 | 12/2003 | Lund | |
| 2005/0271462 A1 | 12/2005 | Curtis | |
| 2005/0278038 A1 | 12/2005 | Ikeda | |
| 2007/0260328 A1 | 11/2007 | Bertels et al. | |
| 2009/0043402 A1 | 2/2009 | Slemker | |
| 2010/0036505 A1 | 2/2010 | Hassler | |

(Continued)

FOREIGN PATENT DOCUMENTS

| | | |
|---|---|---|
| GB | 2169207 A | 7/1986 |
| GB | 2274994 A | 8/1994 |
| JP | 8-089519 A * | 4/1996 |
| RU | 2088182 C1 | 8/1997 |

OTHER PUBLICATIONS

JP 7-155343 A (Jun. 20, 1995) English language translation.

(Continued)

*Primary Examiner* — David H Willse

(57) ABSTRACT

A modular prosthesis system that can be inexpensively manufactured using modern technology and advanced polymer materials. The modular prosthesis system will be immediately fit on the residual limb and aligned for optimal gait without specialized tools or labs, alleviating the many steps involved with conventional labor-intensive and costly prosthesis construction. The modular prosthesis system also accommodates the changing in size and shape of the limb, eliminating the need for multiple prostheses and adjustments to an existing prosthesis during the lifetime of an amputee.

16 Claims, 13 Drawing Sheets

U.S. PATENT DOCUMENTS

2010/0274364 A1    10/2010    Pacanowsky et al.
2011/0015761 A1    1/2011    Celebi et al.
2011/0071647 A1    3/2011    Mahon

OTHER PUBLICATIONS

Office Action issued on Apr. 16, 2013 in related U.S. Appl. No. 13/274,146.

Notice of Allowance issued on Apr. 1, 2013 in related U.S. Appl. No. 13/274,130.

Written Opinion and International Search Report issued Mar. 15, 2013 in related International Patent Application No. PCT/US2012/060166.

Written Opinion and International Search Report issued Mar. 29, 2013 in related International Patent Application No. PCT/US2012/060168.

* cited by examiner

MODULAR PROSTHESIS SYSTEM

STATEMENT REGARDING FEDERALLY SPONSORED RESEARCH OR DEVELOPMENT

This invention was made with government support under NIH Grant 2R42HD069067-02 awarded by the National Institutes of Health. The government has certain rights in the invention.

FIELD OF INVENTION

The present invention relates to the field of prostheses, and more particularly to a modular prosthesis system.

GLOSSARY

Figure 1:
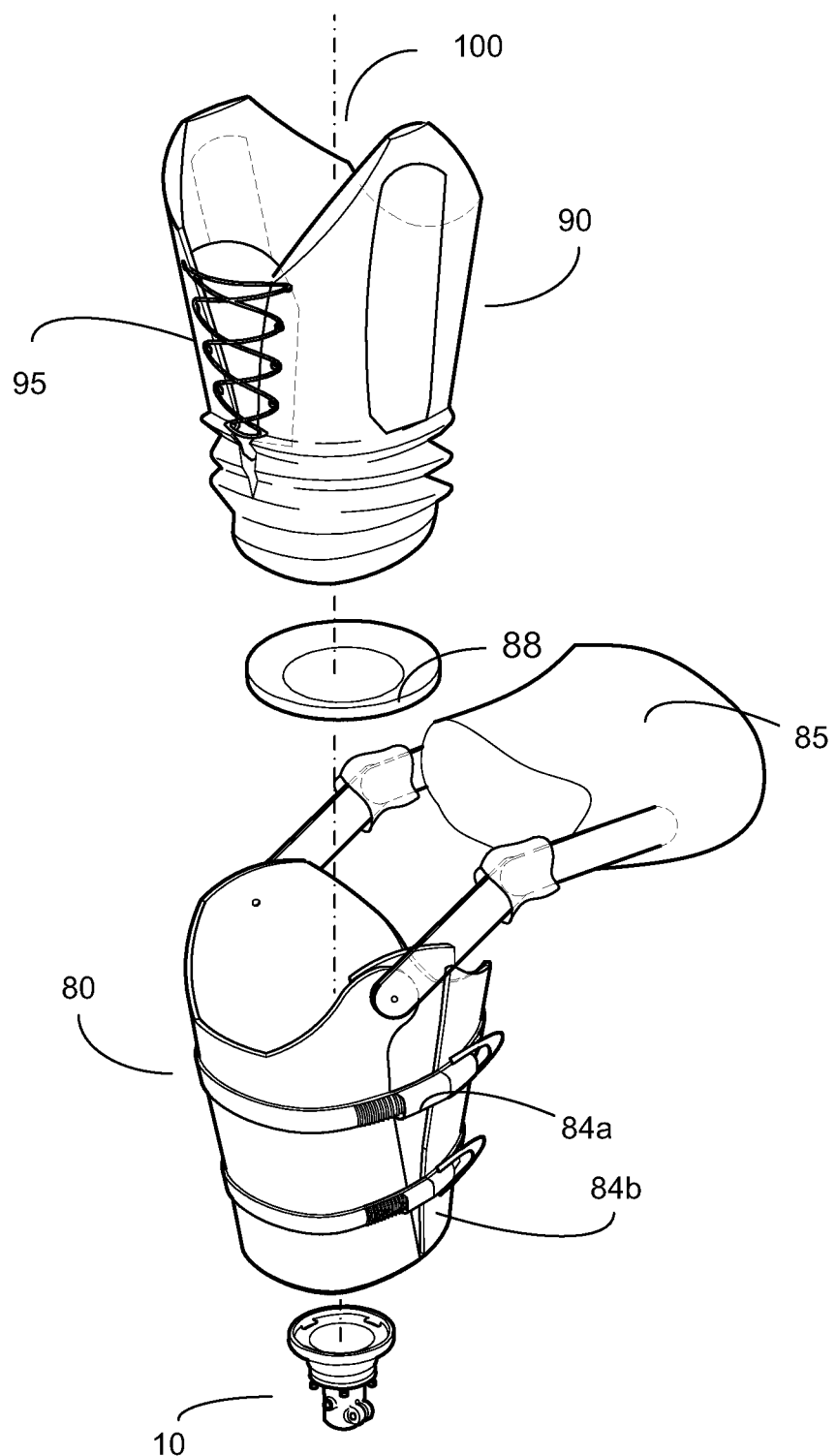
FIG. 1 illustrates an exploded view of an exemplary embodiment of a modular prosthesis system.

As used herein, the term "dynamic stress point profile" refers to the unique anatomic and physiologic characteristics of an amputee's residual limb which govern the distribution of forces and stresses on the residual limb during activity.

As used herein, the term "grid pattern" refers to a configuration of uniformly repeating shapes arranged in a network of uniformly spaced horizontal and perpendicular lines.

As used herein, the term "modular prosthesis system" refers to a prosthesis system comprised of components that are interchangeable and designed to function together as a unit. Components of a modular prosthesis system may be off-the-shelf or custom-made.

As used herein, the term "pivotal side joints" refers to components of a suspension system that allow an amputee to bend his or her knee while wearing the prosthesis. Pivotal side joints may be comprised of one or more straight, curved, or irregular-shaped components. The components of a multi-component pivotal side joint are connected at a pivot point, the location of which may vary.

As used herein, the term "shank" refers to a tubular component attached to a connector at one end and a prosthetic foot at the other end.

As used herein, the term "supporting component" refers to a component which provides additional foundation for bearing the weight of the central plate and upper assembly of a connector as well as the weight of the amputee.

As used herein, the term "washer" refers to a component which distributes pressure from another component and provides a firm attachment through friction to prevent movement of the component. For example, a washer placed under a threaded fastener will distribute the pressure from the head of the fastener and prevent movement of the fastener.

BACKGROUND

Over 150,000 amputations occur in the United States annually. Amputations are rising in frequency due to diabetes and peripheral vascular disease. The transtibial level of amputation is the most frequently performed.

A transtibial amputation is an amputation of the lower limb below the knee. A transtibial prosthesis is an artificial limb that replaces the portion of the leg below the knee that is missing. The shape of the residual limb varies for each individual and generally requires a custom-fitted prosthesis. A custom-fitted prosthesis that is comfortable is difficult to fabricate and is costly.

The initial cost of a conventional prosthesis for a transtibial amputee typically ranges from $6000 to $10,000. In addition, there are additional costs to ensure the comfort and functionality of the device. The present state of prosthesis fabrication often requires three or more visits to the prosthetist and there are multiple steps in the fabrication process. First, a cast mold of the residual limb is made and a positive cast that resembles the residual limb is generated. Then, a prosthetic socket is built to custom-fit over the positive cast. Sometimes a check or temporary socket is made to insure a better fit. Typical fabrication techniques require specialized facilities. Generally, the final prosthesis requires post-fabrication adjustments as the residual limb tissue changes over time.

Recent advancements have been made in the field of prosthetic devices. However, devices such as computerized knee mechanisms and energy storing feet are costly and beyond the economic means of the majority of prosthetic users, particularly those in nations outside the United States.

Attempts have been made in the prior art to develop prosthesis systems that can be globally manufactured and distributed. These prosthesis systems, however, have several limitations. They are difficult to fabricate and require specialized facilities for initial manufacturing (e.g., casting) and subsequent adjustments. These systems all require expertise and consulting support that is not widely available. In particular, the socket (i.e., the portion of the prosthesis into which the residual limb fits), socket attachment, and alignment aspects of the device seem to be a common problematic area of development.

It is desirable to create a prosthetic device which eliminates the need for complex fabrication and specialized tools or labs, and which can be economically manufactured and distributed on a global basis.

SUMMARY OF THE INVENTION

The present invention is a modular prosthesis system comprised of a connector, socket, and liner. The connector is made up of two main components: an upper assembly which is secured to the socket and a lower assembly which is secured around a shank. The design of the connector allows for angular adjustment which ensures proper positioning and alignment of the foot. In addition, the socket and liner include tightening components, resulting in a prosthesis that may be fit to any residual limb and which can accommodate long-term and daily changes in the amputee and residual limb as well as other aspects of an amputee's dynamic stress distribution profile.

DETAILED DESCRIPTION OF INVENTION

For the purpose of promoting an understanding of the present invention, references are made in the text to exemplary embodiments of a modular prosthesis system, only some of which are described herein. It should be understood that no limitations on the scope of the invention are intended by describing these exemplary embodiments. One of ordinary skill in the art will readily appreciate that alternate but functionally equivalent materials, components, and designs may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead, emphasis has been placed upon illustrating the principles of the invention. In addition, in the embodiments depicted herein, like reference numerals in the various drawings refer to identical or near identical structural elements.

Moreover, the terms "substantially" or "approximately" as used herein may be applied to modify any quantitative representation that could permissibly vary without resulting in a change in the basic function to which it is related.

Figure 10:
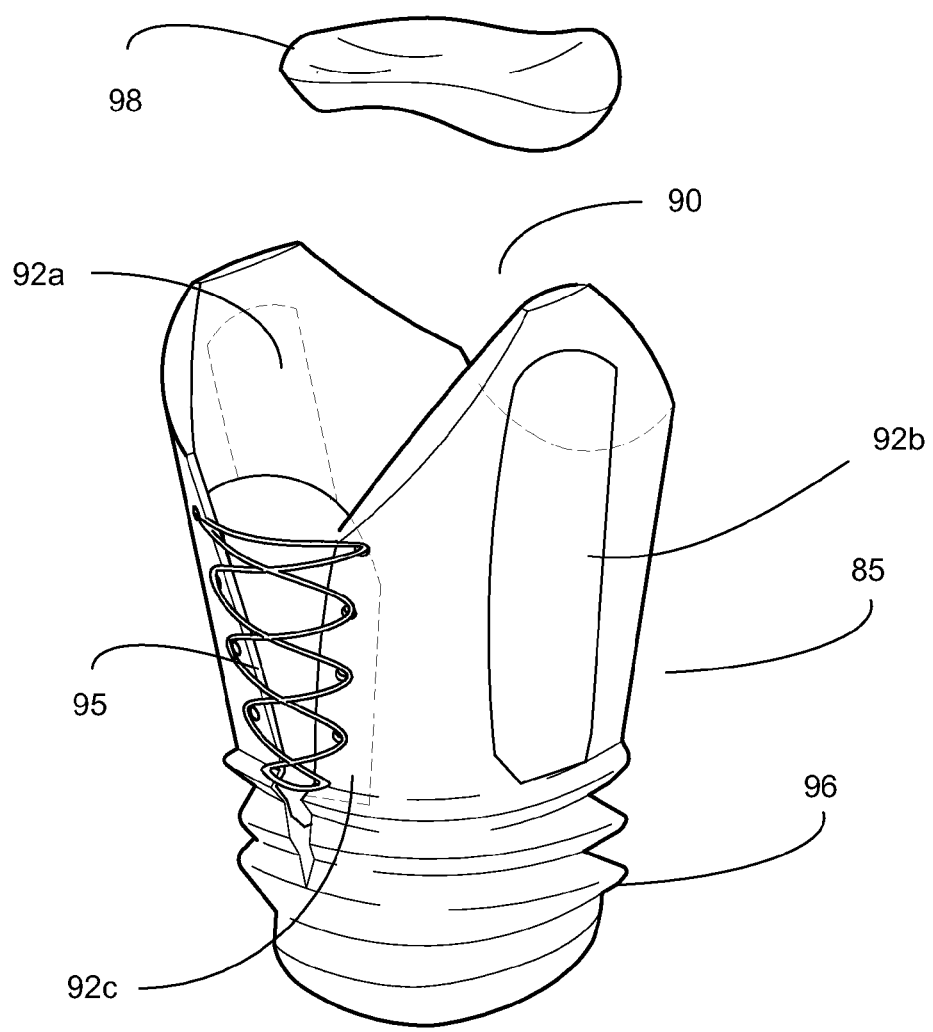
FIG. 10 illustrates a perspective view of an exemplary embodiment of a liner for a modular prosthesis system.
Figure 11:
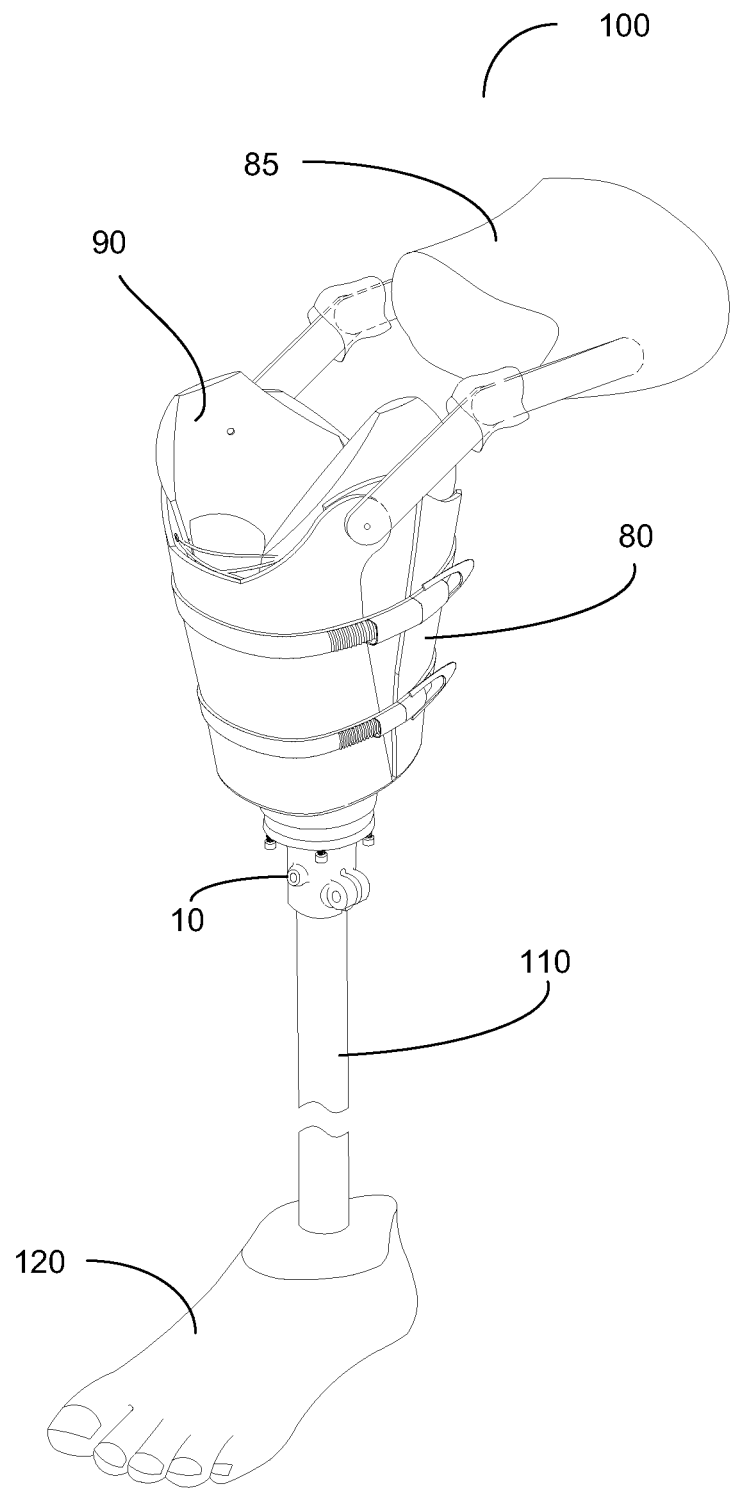
FIG. 11 illustrates a perspective view of an exemplary embodiment of an assembled modular prosthesis system.

FIG. 1 illustrates an exploded view of an exemplary embodiment of modular prosthesis system 100 comprised of connector 10, socket 80 with suspension system 85 (see FIG. 9), liner 90 (see FIG. 10), and shank 110 (see FIG. 11). In the embodiment shown, socket 80 and liner 90 include tightening components 84a, 84b and 95, respectively. Also visible in the embodiment shown is optional padding insert 88 which is placed at the bottom of socket 80 to support liner 90.

Figure 2:
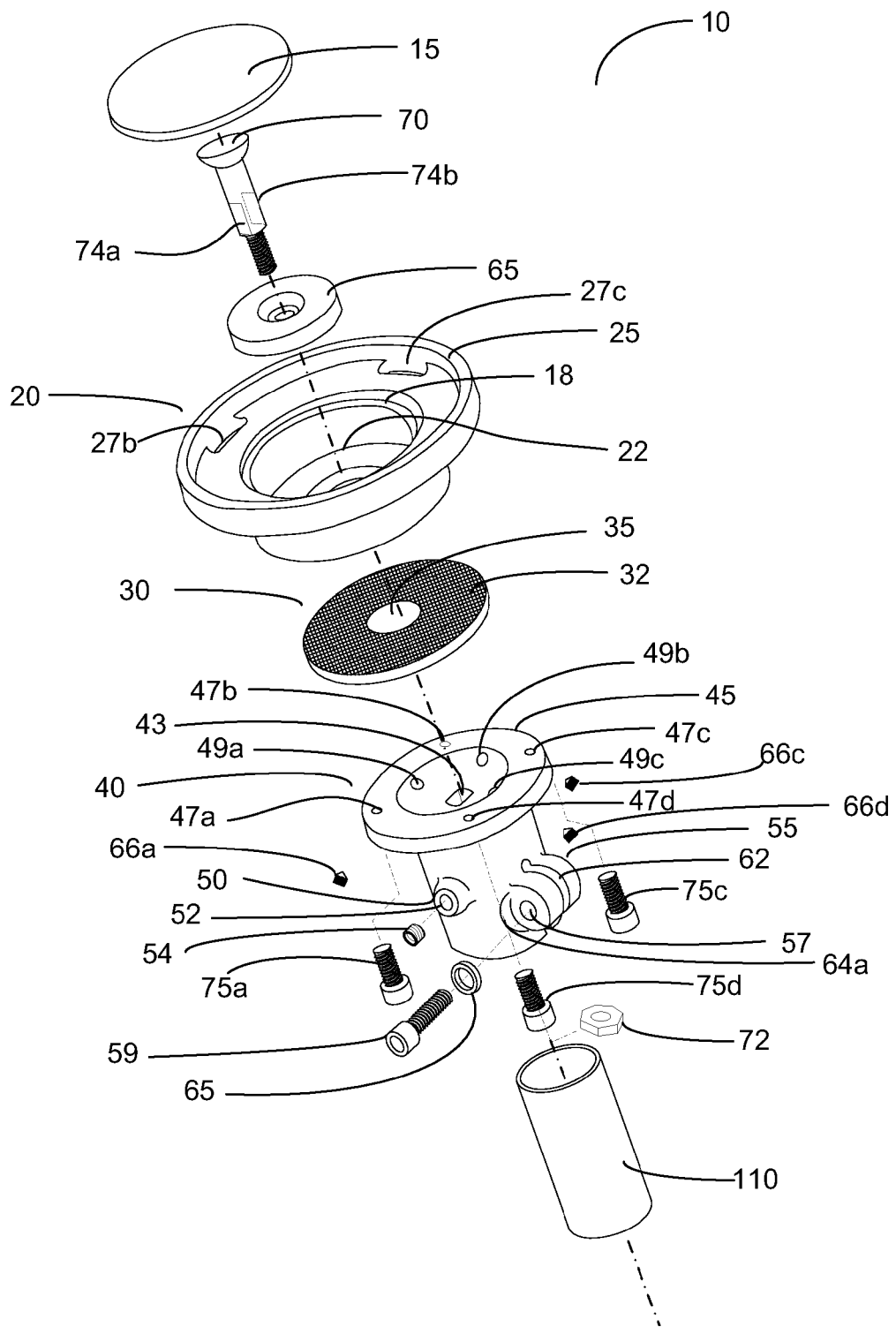
FIG. 2 illustrates an exploded view of an exemplary embodiment of a connector component for a modular prosthesis system.

FIG. 2 illustrates an exploded view of an exemplary embodiment of connector 10 for modular prosthesis system 100. In the embodiment shown, connector 10 is comprised of upper assembly 20, central plate 30, and lower assembly 40.

Upper assembly 20 is a tubular component with socket flange 25. In the embodiment shown, socket flange 25 is cup-shaped with a flat top surface. At the interface of socket flange 25 and the lower tubular portion of upper assembly 20 is ridge 18 for receiving and supporting cover 15. Socket flange 25 further includes apertures 27a, 27b, 27c, 27d (27a, 27d not visible) for inserting securing components 29a, 29b, 29c, 29d (not visible) used to secure connector 10 to socket 80. In the embodiment shown, apertures 27a, 27b, 27c, 27d are oval-shaped and are located near the edge of socket flange 25. In various other embodiments, apertures 27a, 27b, 27c, 27d are eliminated and socket 80 is secured to connector 10 in an alternate way. For example, one or more bolts or other fasteners may be threaded through apertures positioned on a substantially horizontal surface of upper assembly 20 and corresponding apertures on socket 80 (see FIG. 12).

Centered in the bottom of upper assembly 20 is aperture 22 for tapered shoulder screw 70. In the embodiment shown, aperture 22 is round and has a diameter that is substantially larger than the diameter of tapered shoulder screw 70.

Central plate 30 is located between upper assembly 20 and lower assembly 40. The top surface of central plate 30 has raised grid pattern 32. In the embodiment shown, raised grid pattern 32 is uniform and has a plurality of raised protuberances in the shape of isosceles trapezoids. The bottom surface of upper assembly 20 has recessed grid pattern 28 (see FIGS. 3 and 4) that corresponds to raised grid pattern 32 on the top surface of central plate 30. Corresponding grid patterns 28, 32 on the bottom surface of upper assembly 20 and the top surface of central plate 30, respectively, allow for forward and backward adjustment and side-to-side adjustment.

In the embodiment shown, the bottom surface of central plate 30 has a rounded protuberance 37 (see FIG. 6) which corresponds to the shape of the upper surface of lower assembly 40. Central plate 30 further includes aperture 35 for tapered shoulder screw 70. In the embodiment shown, aperture 35 is round and has a diameter that is substantially larger than the diameter of the shank of tapered shoulder screw 70, but smaller than the diameter of aperture 22 in upper assembly 20.

Lower assembly 40 is a tubular component with central plate flange 45. In the embodiment shown, the outer edge of the top surface of central plate flange 45 is flat, while the center portion of the top surface of central plate flange 45 is concave to accommodate rounded protuberance 37 of central plate 30.

The flattened portion of the top surface of central plate flange 45 includes a plurality of apertures 47a, 47b, 47c, 47d for central plate supporting components 75a, 75b, 75c, 75d (75d not visible). In the center of central plate flange 45 is aperture 43 for tapered shoulder screw 70. In the embodiment shown, aperture 43 is oval-shaped to accommodate and secure tapered shoulder screw 70.

In the embodiment shown, the outer edge of concave portion on the top surface of central plate flange 45 further includes a plurality of apertures 49a, 49b, 49c, 49d (49d not visible) for insertion of set screws 66a, 66b, 66c, 66d (66b not visible). Apertures 49a, 49b, 49c, 49d pass completely through central plate flange 45 and set screws 66a, 66b, 66c, 66d help to firmly anchor connector 10 once the final position has been attained. In the embodiment shown, set screws 66a, 66b, 66c, 66d are coin point set screws; however, in other embodiments may be another type of set screw known in the art (e.g., domed point, cup point, dog point).

In the embodiment shown, upper assembly 20 further includes depressions 51a, 51b, 51c, 51d (see FIGS. 3 and 4) located on the top of the tubular portion of lower assembly 40 just under apertures 49a, 49b, 49c, 49d. Depressions 51a, 51b, 51c, 51d provide a space which allows a tool (e.g., a Hex driver) to be used to insert set screws 66a, 66b, 66c, 66d.

In addition, one side of tubular portion of lower assembly 40 further includes raised surface 50 which has aperture 52 for insertion of set screw 68. Aperture 52 passes completely through the side of lower assembly 40 and when set screw 54 is inserted, the end of set screw 54 crosses the plane of the inner surface of lower assembly 40 and bumps against shank 110 (not shown). In the embodiment shown, the top of raised surface 50 is flat; however, in other embodiments, the top of raised surface 50 may have slight curvature, mimicking the contours of lower assembly 40. In the embodiment shown, set screw 54 is a cone point set screw.

In the embodiment shown, lower assembly 40 further includes protuberance 55 having apertures 57 for insertion of shank securing component 59. Protuberance 55 is rounded and extends perpendicularly outward from lower assembly 40. In the embodiment shown, lower assembly 40 further includes groove 60 which starts at the bottom of lower assembly 40 and extends to approximately the center of lower assembly 40, cutting protuberance 50 in half. In the embodiment shown, lower assembly 40 further includes depressions 64a, 64b (64b not visible) in lower assembly 40 on each side of protuberance 55. Depressions 64a, 64b provide a space which allows a tool (e.g., wrench, socket wrench) to be used to tighten shank securing component 59.

In the embodiment shown, shank securing component 59 is comprised of a bolt and nut; the bolt is inserted through aperture 57 and the nut is threaded onto the end of the screw and tightened, securing lower assembly 40 to shank 110 and preventing lower assembly 40 from rotating around shank 110.

In the embodiment shown, shank 110 has a diameter of 30 mm; however, in other embodiments, lower assembly 40 may be designed to accommodate shanks of varying diameters. In an exemplary embodiment, shank 110 will include a connector at the bottom which allows various types of feet known in the art, such as an SACH foot or the NIAGRA foot, to be connected to shank 110. In an exemplary embodiment, the length of shank 110 is adjustable, eliminating the need to cut shank 110 to a length sized for each amputee.

Tapered shoulder screw 70 is inserted through aperture 22 in upper assembly 20, aperture 35 in central plate 30, and aperture 43 in lower assembly 40. When tapered shoulder screw 70 is positioned, the threaded end of tapered shoulder screw 70 extends into lower assembly 40. Nut 72 is threaded onto the treaded end of tapered shoulder screw 70 and tightened, securing upper assembly 20, central plate 30, and lower assembly 40 together.

In the embodiment shown, nut 72 is a K-nut, that is, a nut with an attached, free-spinning washer. In the embodiment shown, the washer is an external star washer. The use of a K-nut provides maximum torsional resistance and prevents loosening caused by vibration.

In the embodiment shown, tapered shoulder screw 70 is inserted through washer 65 before tapered shoulder screw 70 is inserted through aperture 22 in upper assembly. Washer 65 has a larger diameter than aperture 22 covering aperture 22 and preventing tapered shoulder screw 70 from directly touching upper assembly 20. Washer 65 distributes the load of tapered shoulder screw 70.

In the embodiment shown, tapered shoulder screw 70 is a shoulder screw with a flat, tapered head and machined grooves 74a, 74b cut on opposite sides of tapered shoulder screw 70. Machined grooves 74a, 74b lock tapered shoulder screw 70 automatically into place inside oval-shaped aperture 43 in lower assembly 40, allowing tapered shoulder screw 70 to be tightened from one end.

In the embodiment shown, the bottom of washer 65 is flat while the top of washer 65 has a beveled outer edge. The edges of the aperture in the center of washer are also beveled. The bevel angle is greater on the top of washer 65 to accommodate the tapered head of tapered shoulder screw 70. When washer 65 is used, only a small portion of the head of tapered shoulder screw 70 is visible above washer 65.

The large diameters (i.e., diameters substantially larger than the diameter of the shoulder of tapered shoulder screw 70) of aperture 22 in upper assembly 20 and aperture 35 in central plate 30, the oval shape of aperture 43 in lower assembly 40, rounded protuberance 37 of central plate 30 and corresponding concave center portion of top surface of lower assembly 40, and tapered shoulder screw 70 allow for angular adjustment of upper assembly 20 and central plate 30 in relationship to lower assembly 40. The ability to angularly adjust connector 10 allows connector 10 to accommodate various stump configurations, providing additional comfort to the amputee.

Once upper assembly 20, central plate 30, and lower assembly 40 are correctly positioned, nut 72 is tightened on tapered shoulder screw 70 and central plate supporting components 75a, 75b, 75c, 75d are inserted into apertures 47a, 47b, 47c, 47d from the bottom and are tightened until the ends of central plate supporting components 75a, 75b, 75c, 75d press against the bottom of central plate 30, supporting central plate 30 and upper assembly 20 and further securing upper assembly 20, central plate 30, and lower assembly 40 together.

Cover 15 is placed on upper assembly 20 so that it rests on ridge 18 of upper assembly 20, covering tapered shoulder screw 70 and washer 65. When cover 15 is positioned, the surface of cover 15 is flush with the inside surface of socket flange 25.

In the embodiment shown, cover 15 and ridge 18 are shown for ease of illustration. In various other embodiments, ridge 18 and cover 15 are omitted and the inner surface of socket flange 25 is a single piece.

In the embodiment shown, upper assembly 20, central plate 30, lower assembly 40, and cover 15 are comprised of polyphthalamide (i.e., PPA or high performance polyamide); however, in various other embodiments may be comprised of other thermoplastics/synthetic resins, such as nylon, acrylonitrile butadiene styrene (ABS), polypropylene, polyamide-imide, polybenzimidazole (PBI), polybutylene (PB-1) or combinations thereof, or any other suitable non-metal material.

Figure 3:
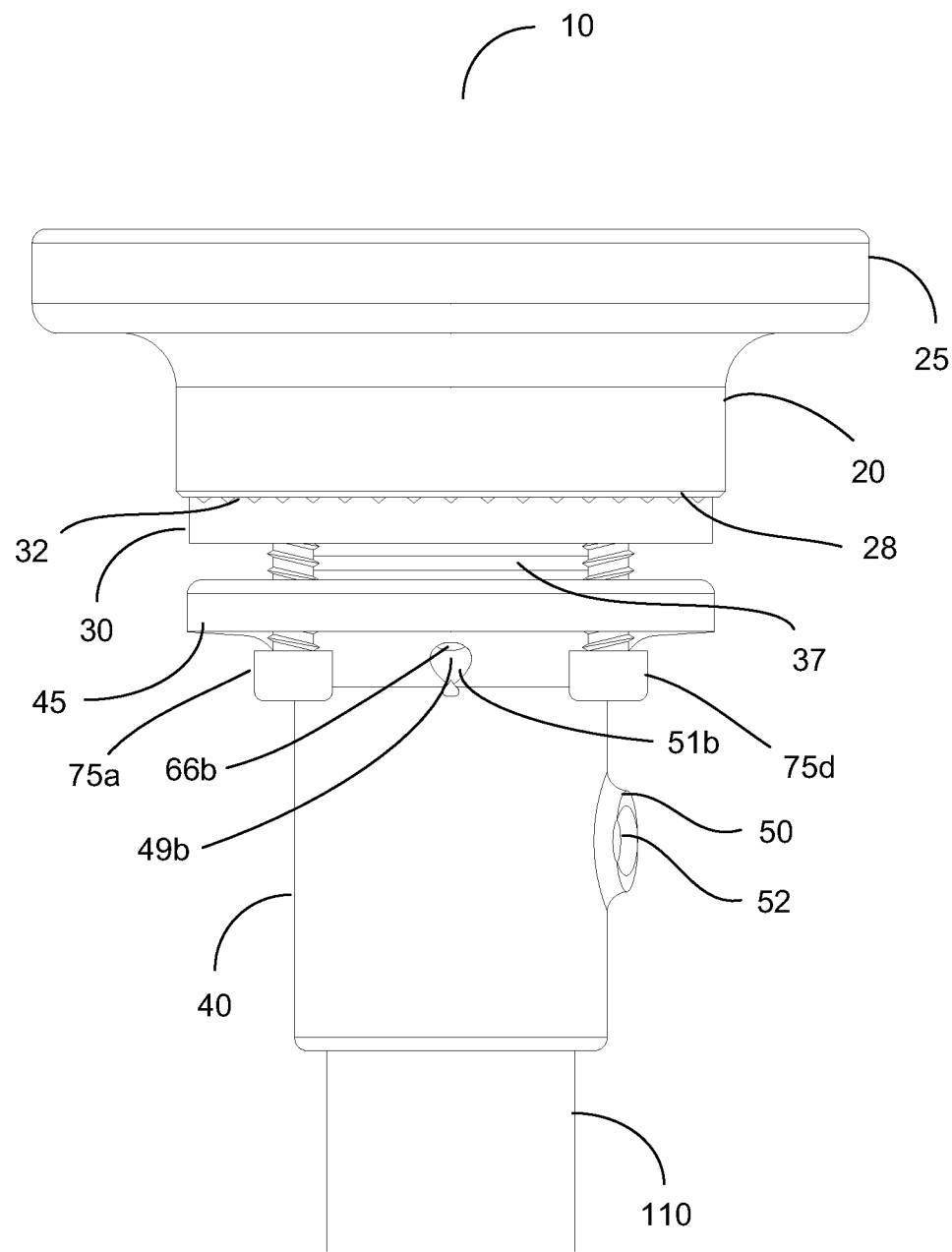
FIG. 3 illustrates a front view of an exemplary embodiment of a connector for a modular prosthesis system.

FIG. 3 illustrates a front view of an exemplary embodiment of connector 10 for modular prosthesis system 100. Visible in FIG. 3 are upper assembly 20, including socket flange 25 and recessed grid pattern 28; central plate 30, including raised grid pattern 32 and rounded protuberance 37; lower assembly 40, including central plate flange 45, aperture 49b, depression 51b, raised surface 50, and aperture 52; set screw 66b; central plate supporting components 75a, 75d; and shank 110.

Figure 4:
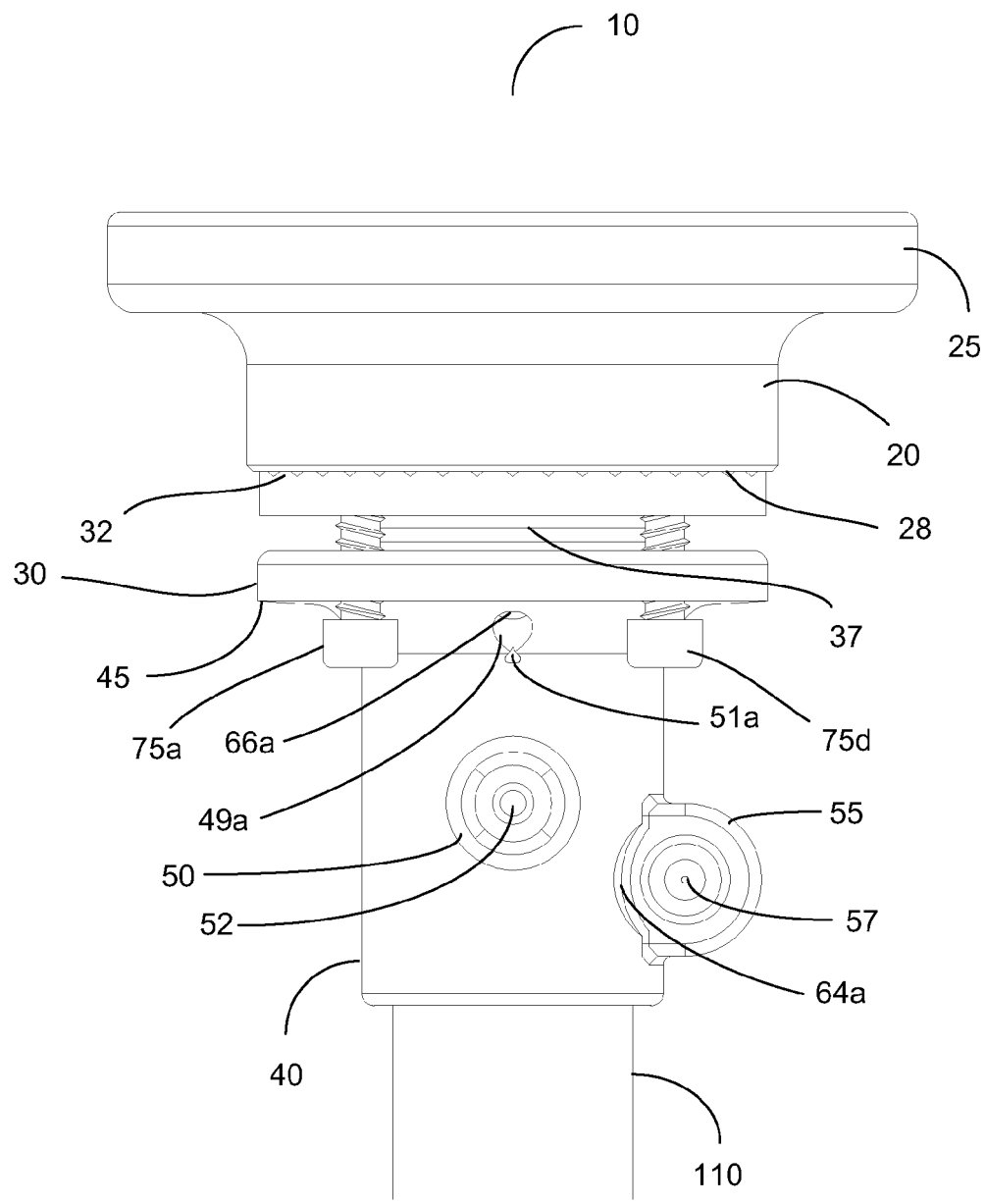
FIG. 4 illustrates a side view of an exemplary embodiment of a connector for a modular prosthesis system.

FIG. 4 illustrates a side view of an exemplary embodiment of connector 10 for modular prosthesis system 100. Visible in FIG. 4 are upper assembly 20, including socket flange 25 and recessed grid pattern 28; central plate 30, including raised grid pattern 32 and rounded protuberance 37; lower assembly 40, including central plate flange 45, aperture 49a, depression 51a, raised surface 50, aperture 52, protuberance 55, aperture 57, and depression 64a; set screw 66a; central plate supporting components 75a, 75d; and shank 110.

Figure 5:
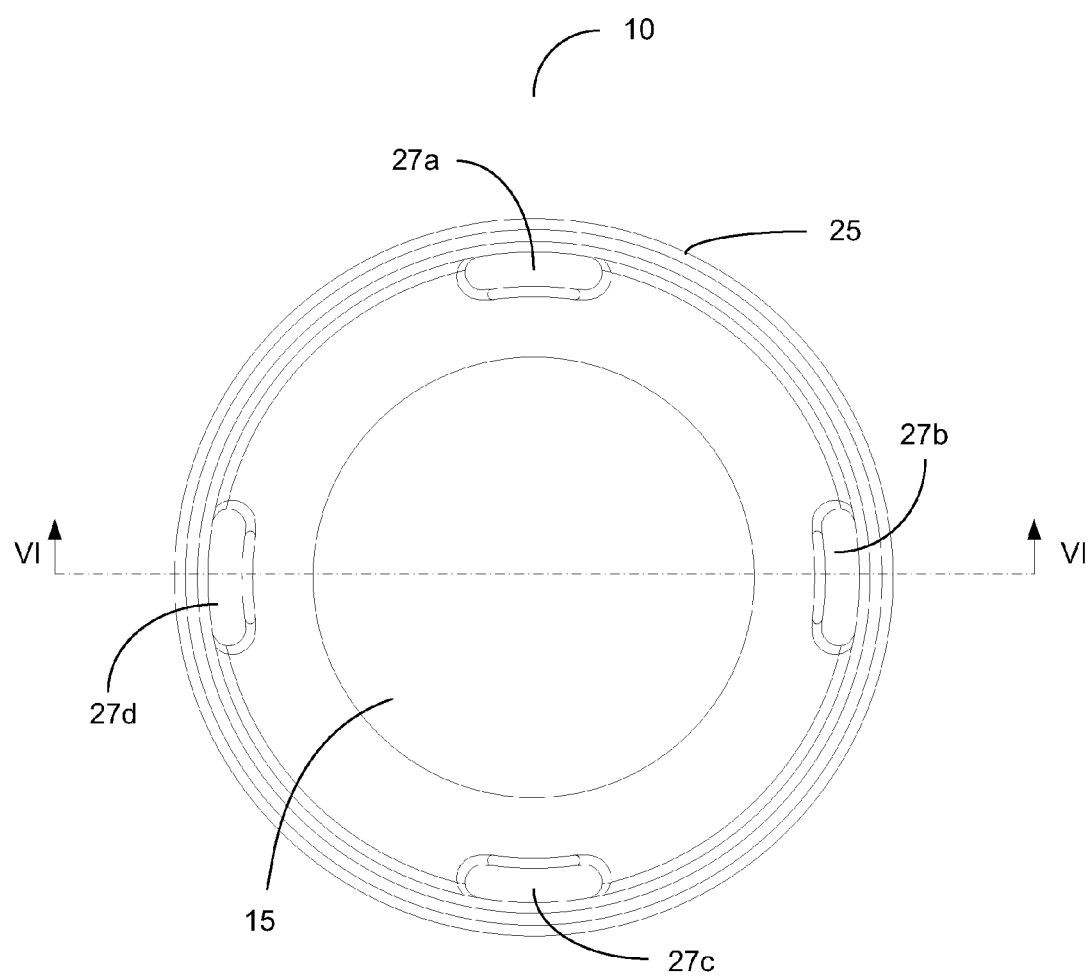
FIG. 5 illustrates a top view of an exemplary embodiment of a connector for a modular prosthesis system.

FIG. 5 illustrates a top view of an exemplary embodiment of connector 10 for modular prosthesis system 100. Visible in FIG. 5 are socket flange 25 of upper assembly 20, cover 15, and apertures 27a, 27b, 27c, 27d for securing components 29a, 29b, 29c, 29d (not visible), which are used to secure connector 10 to socket 80 (not visible).

Figure 6:
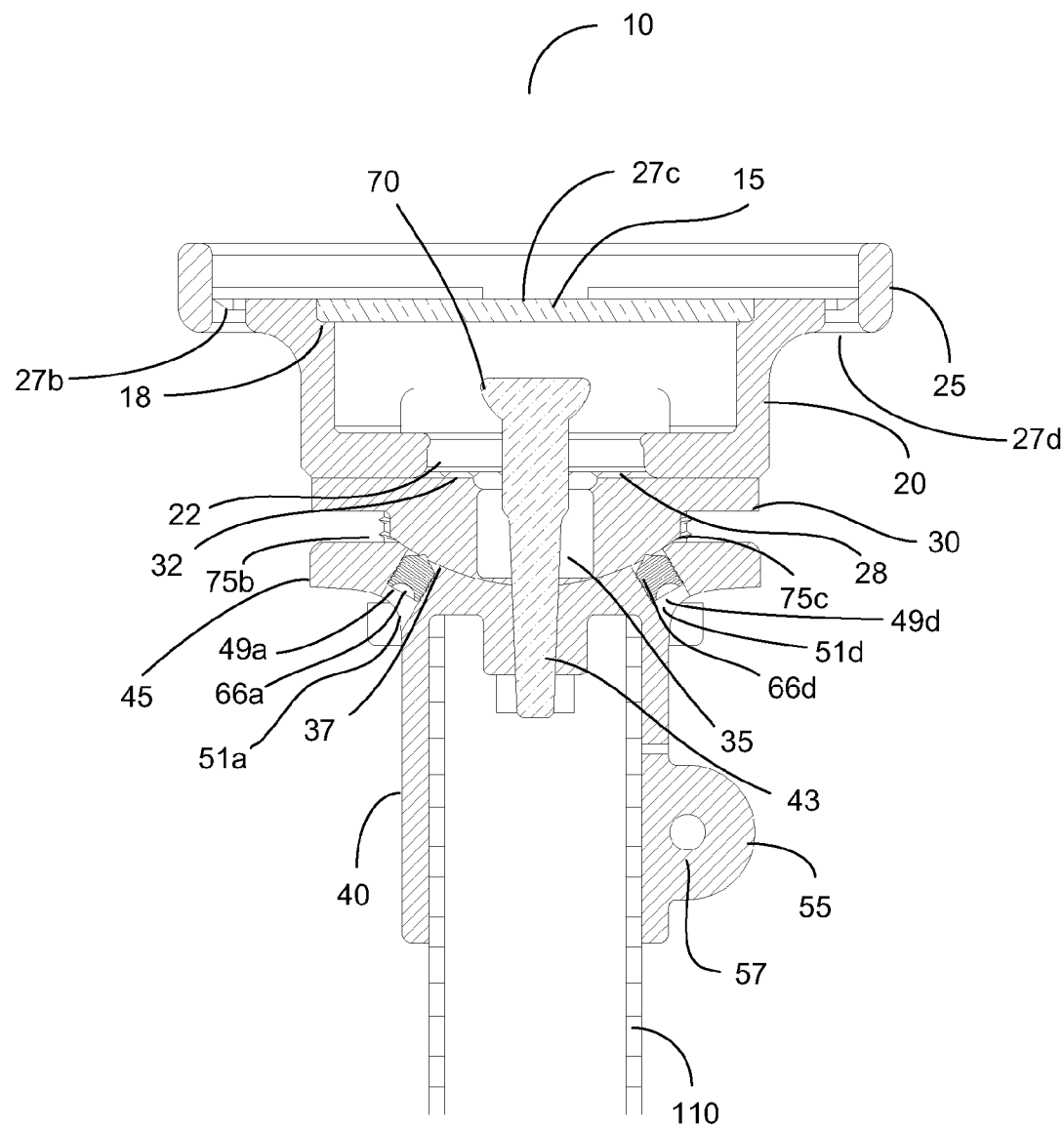
FIG. 6 illustrates a sectional view of an exemplary embodiment of a connector for a modular prosthesis system.

FIG. 6 illustrates a sectional view of an exemplary embodiment of connector 10 for modular prosthesis system 100 taken along line VI of FIG. 5. Visible in FIG. 6 are cover 15; upper assembly 20, including aperture 22, socket flange 25, recessed grid pattern 28, aperture 27d, and ridge 18; central plate 30, including aperture 35, raised grid pattern 32, and rounded protuberance 37; lower assembly 40, including aperture 43, central plate flange 45, aperture 49a, 49d, depression 51a, 51d, and protuberance 55; set screws 66a, 66d; central plate supporting components 75b, 75c; tapered shoulder screw 70, and shank 110.

Figure 7A:
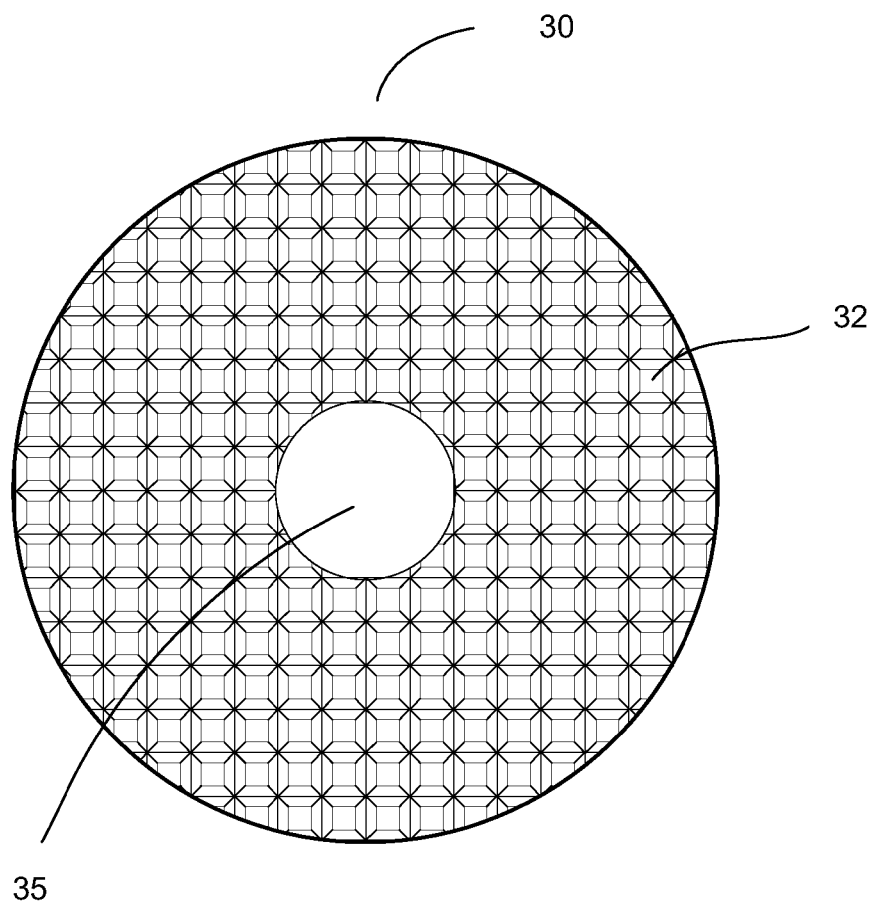
FIG. 7a illustrates a top view of an exemplary embodiment of a central plate of a connector.

FIG. 7a illustrates a top view of an exemplary embodiment of central plate 30 showing raised grid pattern 32 and aperture 35.

Figure 7B:
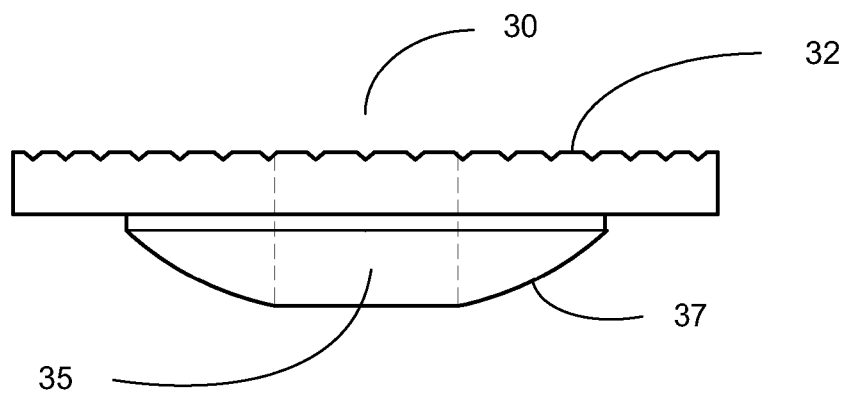
FIG. 7b illustrates a side view of an exemplary embodiment of a central plate of a connector.

FIG. 7b illustrates a side view of an exemplary embodiment of central plate 30 showing raised grid pattern 32, aperture 35, and rounded protuberance 37.

Figure 8A:
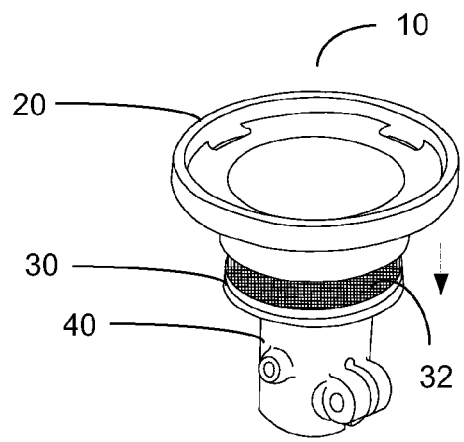
FIGS. 8a, 8b, and 8c illustrate front-back, side-to-side, and angular adjustment of an exemplary embodiment of a connector.
Figure 8B:
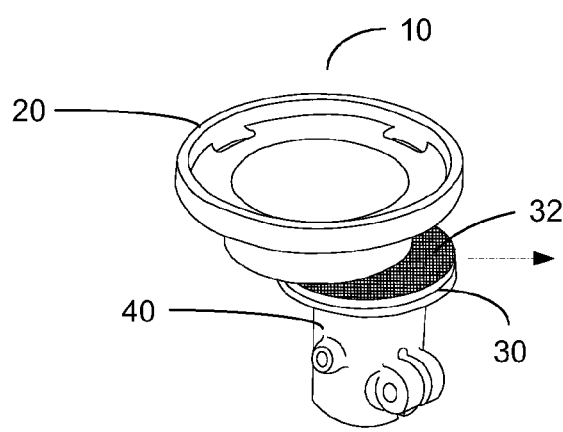
Figure 8C:
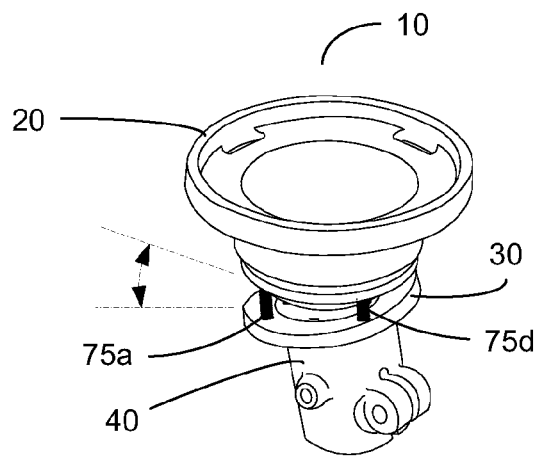

FIGS. 8a, 8b, and 8c illustrate front-back, side-to-side, and angular adjustment of an exemplary embodiment of connector 10, which allow the angle and position of prosthetic foot 120 (FIG. 11) to be changed (e.g., to compensate for foot inset-outset). In FIG. 8a, upper assembly 20 has been shifted backward (i.e., along x-axis) in relation to central plate 30 and lower assembly 40. In FIG. 8b, upper assembly 20 has been shifted sideways (i.e., along y-axis) in relation to central plate 30 and lower assembly 40.

When upper assembly 20 is shifted forward-backward or sideways (i.e., along x- or y-axis) in relation to central plate 30 and lower assembly 40, a portion of recessed grid pattern 28 (not visible) on the lower surface of upper assembly 20 and portion of raised grid pattern 32 on the upper surface of central plate 30 are exposed. The size of aperture 22 in upper assembly 20 and aperture 35 in central plate 30 permit tapered shoulder screw 70 (not visible) to be angled when upper assembly 20 is shifted forward-backward and/or sideways in relation to central plate 30 and lower assembly 40, ensuring that upper assembly 20, central plate 30, and lower assembly 40 are secure.

In FIG. 8c, upper assembly 20 and central plate 30 are in tilted in relation to lower assembly 40 so that central plate 30 and central plate flange 45 on lower assembly 40 are no longer parallel. The concave center portion of the top surface of lower assembly 40 allows rounded protuberance 37 on the bottom of central plate 30 to tilt, allowing for angular adjustment of upper assembly 20 and central plate 30. When upper assembly 20 and central plate 30 are positioned at the desired angle, central plate supporting components 75a, 75b, 75c, 75d are tightened, securing lower assembly 40 to upper assembly 20 and central plate 30.

In the embodiment shown, connector 10 is capable of being adjusted in one or more directions concurrently, allowing for maximum adjustment of connector 10 to specifically accommodate each amputee's residual limb and gait. For example, connector 10 may be adjusted front-back, side-to-side, and angled. In other embodiments, connector 10 may be capable of only one type of adjustment (e.g., angular).

Figure 9A:
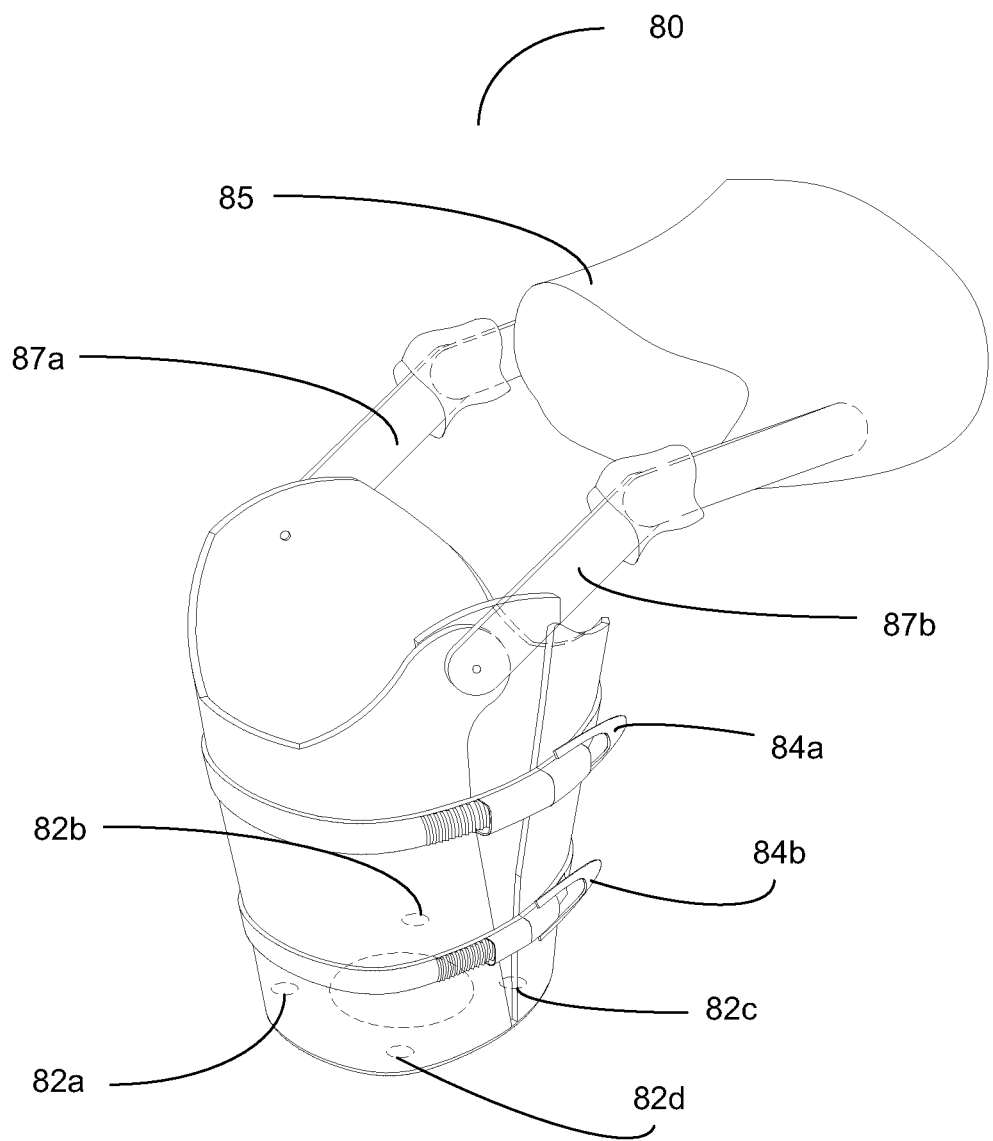
FIGS. 9a and 9b illustrate perspective views of exemplary embodiments of a socket for a modular prosthesis system.
Figure 9B:
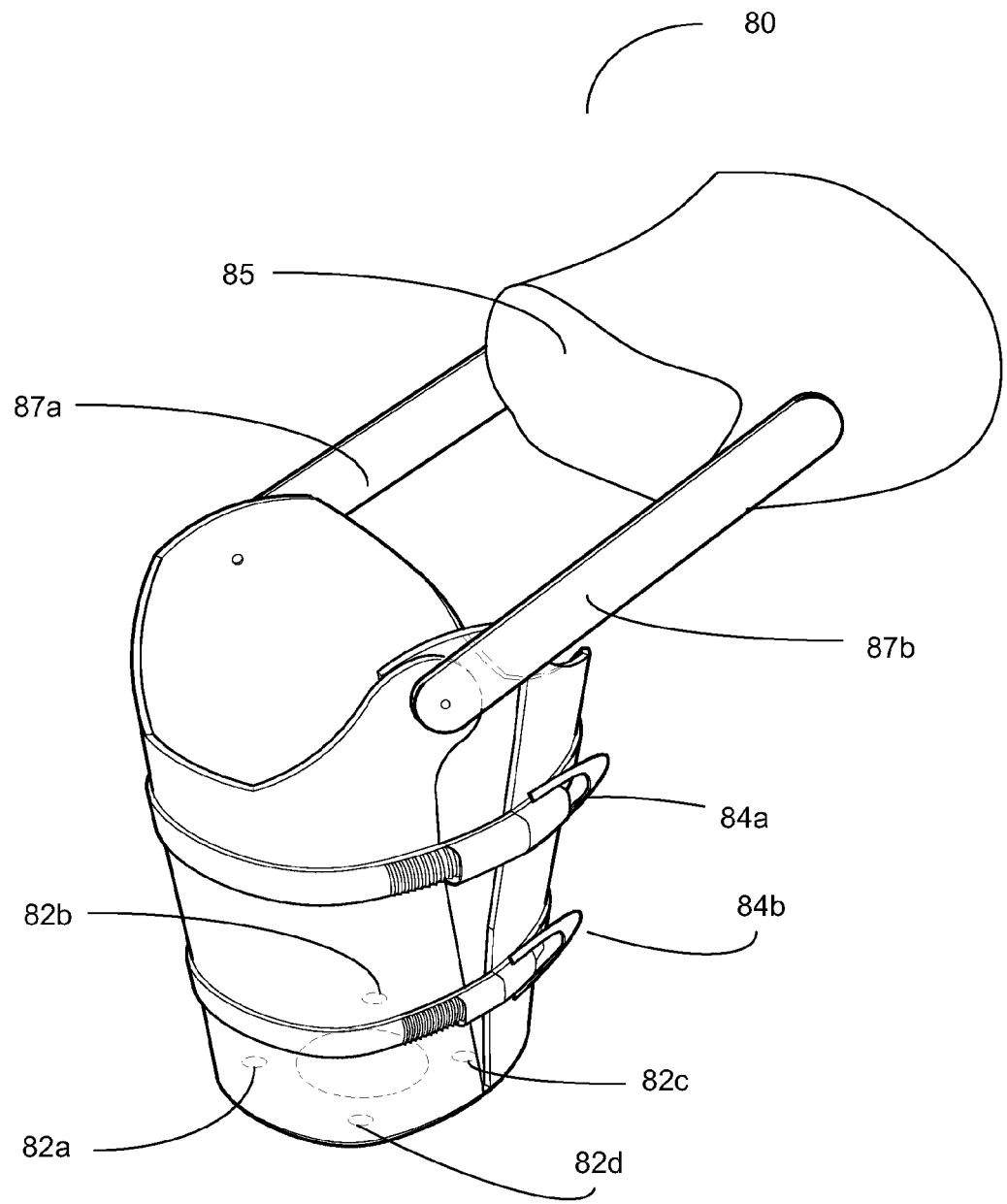

FIGS. 9a and 9b illustrate perspective views of exemplary embodiments of socket 80 for modular prosthesis system 100. Socket 80 includes tightening components 84a, 84b, which allow the tension in socket 80 to be adjusted by each amputee. In the embodiment shown, socket tightening components 84a, 84b are buckle assemblies.

In the embodiment shown, socket 80 further includes suspension system 85 with optional pivotal side joints 87a, 87b. Suspension system 85 secures the prosthesis on the amputee's residual limb. The inclusion of pivotal side joints 87a, 87b allows the amputee to move his or her knee more freely with less hindrance from the prosthesis. In various other embodiments, suspension system 85 may vary. For example, suspension system 85 may be comprised of a roll-on neoprene sleeve with an adjustable strap that goes around the amputee's thigh and one or more length-adjustable straps that connect the sleeve to socket 80.

In FIG. 9a, optional pivotal side joints 87a, 87b are comprised of two pieces connected at a joint. In various embodiments, the joint may be located further from or closer to suspension system 85. In FIG. 9b, optional pivotal side joints 87a, 87b are comprised of a single straight piece. In various embodiments, there may be fewer or more joints, the pieces may be of varying length, and/or curved or irregularly-shaped.

In various other embodiments, there may be more or socket tightening components 84a, 84b and/or the type of tightening components may vary. For example, socket 80 may include laces or one or more straps secured by hook-and-loop fastener or another means.

Also visible are apertures 82a, 82b, 82c, 82d for inserting securing components 29a, 29b, 29c, 29d for securing connector 10 to socket 80.

FIG. 10 illustrates a perspective view of an exemplary embodiment of liner 90 for modular prosthesis system 100. Liner 90 is shaped to fit inside socket 80. In the embodiment shown, liner 90 further includes liner extension component 96 which allows the height of the liner to be adjusted to the length of each amputee's residual limb. In the embodiment shown, liner extension component 96 is a plurality of accordion fabric folds at the bottom portion of liner 90. In various other embodiments, liner extension component 96 may be comprised of adjustable or removable panels or another component that allows the length of liner 90 to be adjusted.

In the embodiment shown, liner 90 has tightening component 95 which allow the tension of liner 90 to be adjusted as the residual limb changes, accommodating long-term or daily changes of the residual limb, as well as allowing the individual amputee to adjust liner 90 to his or her comfort. For example, liner tightening component 95 allows liner 90 to be loosened as a result of swelling of the residual limb. In the embodiment shown, liner tightening component 95 is laces. In various other embodiments, liner tightening component 95 may include one or more adjustable straps.

In the embodiment shown, liner 90 includes stress distribution panels 92a, 92b secured to the outer surface of the sides of liner 90 and stress distribution panels 92c, 92d (92d not visible) secured to the outer surface of the front and back of liner 90. Stress distribution panels 92a, 92b, 92c, 92d help to distribute pressure and shear stresses. In the embodiment shown, stress distribution panels 92a, 92b are comprised of plastic. In various embodiments, the shape of the stress distribution panels varies depending on the placement of the panel (i.e., the side panels have a shape different than that of front and back panels).

In an exemplary embodiment, liner 90 further includes one or more optional removable padding inserts 98, which can be inserted into liner 90 for further adjustability, allowing liner 90 to accommodate the shape of each individual amputee's residual limb. For example, padding inserts may be inserted into the bottom of liner 90 to accommodate a bony prominence at the end of a residual limb or into the sides of liner 90 to add additional padding in areas that are less pressure tolerant.

Liner 90 is comprised of a soft, comfortable material, such as Pelite or silicone, that doesn't break down the skin of the amputee's residual limb. In various other embodiments, liner 90 may be comprised of a plastic mesh material or other material that allows for breathability for use in warmer climates or during physical activities. In various embodiments, liner 90 may be manufactured by gluing together layers of foam having different durometers.

FIG. 11 illustrates a perspective view of an exemplary embodiment of assembled modular prosthesis system 100. In an exemplary embodiment, modular prosthesis system 100 will include all items and components required for immediate fitting. Connector 10, shank 110, and foot 120 will be one fully adjustable system that readily connects to socket 80 and suspension system 85. Liner 90 is inserted into socket 80. In an exemplary embodiment, modular prosthesis system 100 will include a telescoping shank.

Figure 12:
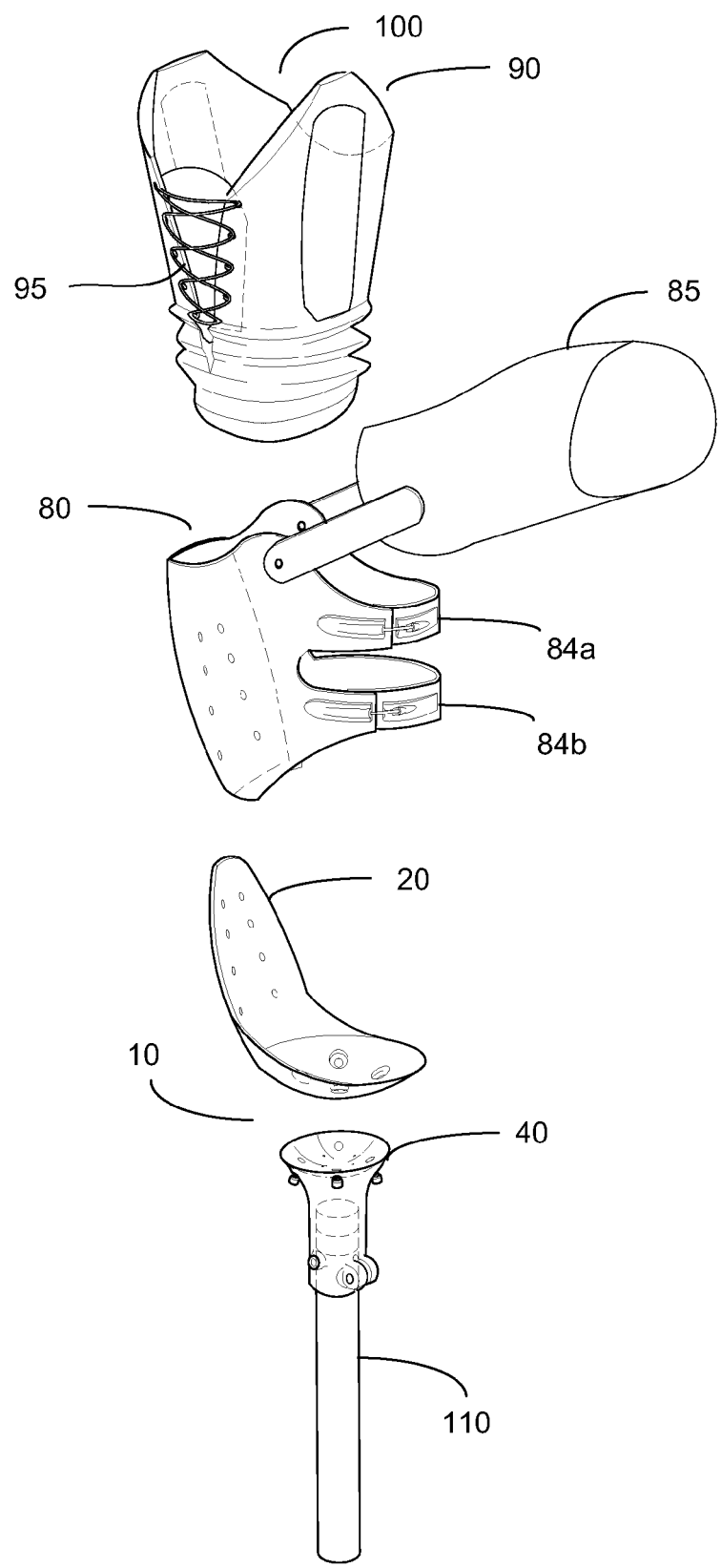
FIG. 12 illustrates an exploded view of a second embodiment of a modular prosthesis system.

FIG. 12 illustrates an exploded view of a second embodiment of modular prosthesis system 100 comprised of socket 80, liner 90, and connector 10. In the embodiment shown, socket 80 and liner 90 include tightening components 84*a*, 84*b*, and 95, respectively, and socket 80 further includes suspension system 85.

In the embodiment shown, connector 10 is comprised of upper assembly 20 and lower assembly 40. Upper assembly 20 is cup-shaped with a rounded bottom and a single elongated side. Lower assembly 40 is tubular-shaped having a flange with a concave center portion and a bottom portion for accepting shank 100. In the embodiment shown, upper assembly 20 is secured to lower assembly 40 by inserting a connecting screw (e.g., a tapered shoulder screw) or another type of fastener into each of the apertures in the rounded bottom of upper assembly 20 and into the apertures in the concave center portion of lower assembly 40. The position of the connecting screws can be adjusted to adjust the tilt between upper assembly 20 and lower assembly 40, allowing the position of the prosthetic foot to be adjusted (e.g., to compensate for foot inset-outset).

In the embodiment shown, the apertures in the bottom of upper assembly 20 are recessed to allow for placement of a washer.

In the embodiment shown, the single elongated side of upper assembly 20 includes a plurality of apertures which correspond to the apertures on socket 80. Socket 80 is secured to upper assembly 20 of connector 10 by threading a screw through two apertures (single row) in socket 80 and upper assembly 20. The plurality of rows of apertures accommodates for height adjustment. For example, for a shorter socket, the amputee would thread screws through the top four apertures of socket 80 and the top four apertures of upper assembly 20 (or any four corresponding apertures). For a longer socket, the amputee would thread screws through the bottom four apertures of socket 80 and the top four apertures of upper assembly 20. For shorter lengths, additional screws could be threaded through corresponding apertures to secure socket 80 and upper assembly more tightly together.

Modular prosthesis system 100 is easily fit to an individual and can be fully constructed and aligned in a reasonable amount of time. No casting or fabrication is required, eliminating the need for specialized tools and centers.

Modular prosthesis system 100 is highly adjustable, making it ideal for growing children, eliminating the need for many prosthetic revisions to insure a comfortable and functional device. In addition, modular prosthesis system 100 can be fit without a prosthetist making it desirable for developing countries, war-torn countries, and for individuals who are without insurance and/or don't have access to a prosthesis. The use of advanced technology and materials allows modular prosthesis system 100 to be economically manufactured and distributed.

What is claimed is:

1. A modular prosthesis system comprised of:
    a prosthetic foot attached to a first end of a shank;
    a connector which securely attaches a socket to a second end of said shank,
        said connector being comprised of:
            a cup-shaped assembly having a rounded bottom and at least one aperture; and
            a tubular assembly having a flanged end and a hollow end, said flanged end integrally formed with a concave surface, said concave surface further including at least one aperture through which a connecting screw may be inserted to connect said cup-shaped assembly to said tubular assembly, said hollow end being further connected to said second end of said shank;
    at least one connecting screw which is inserted through said at least one aperture in said cup-shaped assembly and said at least one aperture in said concave surface to secure said cup-shaped assembly and said tubular assembly together;
    a socket with suspension assembly for securing said socket to a residual limb, said socket having a tubular shape and at least one adjustment component for tightening said socket, said suspension assembly is comprised of a tubular upper leg-engaging member connected to said socket by one or more pivotal side joints;
    wherein said socket is secured to said connector so that the bottom of said socket rests in said cup-shaped assembly; and
    a liner, said liner having a tubular shape with a solid bottom and at least one adjustment component for tightening said liner, said liner is inserted into said socket;
    wherein said at least one adjustment component for tightening said socket and said at least one adjustment component for tightening said liner are capable of being adjusted independently of one another;
    wherein said cup-shaped assembly further includes a vertically elongated side having a plurality of apertures which correspond to a plurality of apertures on said socket to allow for height adjustment.

2. The system of claim 1 which further includes a central plate positioned between said cup-shaped assembly and said tubular assembly.

3. The system of claim 2 wherein said central plate further includes a centered aperture having a diameter that is larger than the diameter of said at least one connecting screw.

4. The system of claim 3 wherein said at least one aperture of said cup-shaped assembly is centered and has a diameter that is larger than the diameter of said at least one connecting screw.

5. The system of claim 4 wherein said at least one aperture of said tubular assembly is oval-shaped.

6. The system of claim 1 which further includes a washer positioned beneath a head of said at least one connecting screw.

7. The system of claim 1 wherein a nut is secured onto a threaded end of said at least one connecting screw.

8. The system of claim 1 wherein said cup-shaped assembly has four apertures adapted to receive a connecting screw.

9. The system of claim 8 wherein said tubular assembly has four apertures adapted to receive a connecting screw.

10. The system of claim 9 wherein said four apertures in said tubular assembly are recessed to allow for placement of a washer.

11. The system of claim 1 where said rounded bottom of said cup-shaped assembly and said concave surface of said tubular assembly allow said cup-shaped assembly to tilt in relation to said tubular assembly so that said cup-shaped assembly is no longer parallel to said flanged end of said tubular assembly.

12. The system of claim 1 which further includes a plurality of supporting components which are threaded through apertures in said flanged end of said tubular assembly until tight against said bottom of said cup-shaped assembly.

13. The system of claim 1 wherein said liner further includes a liner extension component for adjusting the length of said liner.

14. The system of claim 1 wherein said liner further includes a plurality of stress distribution panels.

15. The system of claim 1 which further includes at least one removable padding insert which is adapted to fit within said liner.

16. The system of claim 1 wherein said shank is telescoping.

* * * * *

UNITED STATES PATENT AND TRADEMARK OFFICE
CERTIFICATE OF CORRECTION

PATENT NO. : 8,491,667 B2  
APPLICATION NO. : 13/083403  
DATED : July 23, 2013  
INVENTOR(S) : Timothy R. Dillingham Page 1 of 1

It is certified that error appears in the above-identified patent and that said Letters Patent is hereby corrected as shown below:

In the Specification:

Column 4, line 53 – "insertion of set screw 68" should read as "insertion of set screw 54"

Column 9, line 14 – "accepting shank 100" should read as "accepting shank 110"

Signed and Sealed this
Nineteenth Day of November, 2013

Teresa Stanek Rea
*Deputy Director of the United States Patent and Trademark Office*